US012742195B2

(12) United States Patent
Abecasis et al.

(10) Patent No.: US 12,742,195 B2
(45) Date of Patent: Sep. 22, 2026

(54) GENOTYPING BY SEQUENCING

(71) Applicant: Regeneron Pharmaceuticals, Inc., Tarrytown, NY (US)

(72) Inventors: Goncalo Abecasis, Tarrytown, NY (US); Mathew Barber, Tarrytown, NY (US); William Salerno, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1315 days.

(21) Appl. No.: 17/531,013

(22) Filed: Nov. 19, 2021

(65) Prior Publication Data

US 2022/0154256 A1 May 19, 2022

Related U.S. Application Data

(60) Provisional application No. 63/116,085, filed on Nov. 19, 2020.

(51) Int. Cl.
*C12Q 1/6811* (2018.01)
*C12Q 1/6869* (2018.01)
*C12Q 1/6876* (2018.01)
*G16B 20/20* (2019.01)
*G16B 20/30* (2019.01)

(52) U.S. Cl.
CPC .......... *C12Q 1/6811* (2013.01); *C12Q 1/6869* (2013.01); *C12Q 1/6876* (2013.01); *G16B 20/20* (2019.02); *G16B 20/30* (2019.02)

(58) Field of Classification Search
CPC .. C12Q 1/6809; C12Q 1/6811; C12Q 1/6813; C12Q 1/6874; C12N 15/1006
See application file for complete search history.

(56) References Cited

U.S. PATENT DOCUMENTS 11,624,084 B2 * 4/2023 Teng .................... C12Q 1/6869 435/6.1
2010/0331204 A1 * 12/2010 Jeddeloh ............. C12Q 1/6809 536/23.6
2014/0031240 A1 * 1/2014 Behlke .............. C12N 15/1006 536/24.3
2017/0286594 A1 10/2017 Reid et al.

FOREIGN PATENT DOCUMENTS

WO 2015120280 8/2015

OTHER PUBLICATIONS

Silva-Junior et al., "Desgin and evaluation of a sequence capture system for genome-wide SNP genotyping in highly heterozygous plant genomes: a case study with a keystone neotropical hardwood tree genome", DNA Research, 2018, 25(5), pp. 535-545.

Jakubosky et al., "Doscovery and quality analysis of a comprehensive set of structural variants and short tandem repeats", Nature Communications, 2020, 11(1), pp. 9.

(Continued)

*Primary Examiner* — Lam S Nguyen
(74) *Attorney, Agent, or Firm* — Armstrong Teasdale LLP

(57) ABSTRACT

The present disclosure provides methods for manufacturing nucleic acid probes for genotyping by sequencing, methods for genotyping a DNA sample by sequencing using a set of nucleic acid probes, and systems for carrying out such methods.

22 Claims, 2 Drawing Sheets

(56) References Cited

OTHER PUBLICATIONS

Jiang et al., "A highly robust and optimized sequence-based approach for genetic polymorphism discovery and genotyping in large plant populations", Theoretical and Applied Genetics, 2016, 129(9), pp. 1739-1757.

International Search Report and Written Opinion dated May 16, 2022 for International Patent Application No. PCT/US2021/060085.

* cited by examiner

GENOTYPING BY SEQUENCING

FIELD

The present disclosure is directed, in part, to methods for manufacturing nucleic acid probes for genotyping by sequencing, methods for genotyping a DNA sample by sequencing using a set of nucleic acid probes, and systems for carrying out such methods.

BACKGROUND

Whole genome sequencing involves sequencing the entire genome of an individual. While the cost of whole genome sequencing is decreasing, it is still a considerable cost. The deeper the sequencing, the more costly it is. Different parts of the genome have different levels of focus or interest and so the requirement for deep sequencing varies.

Instead of sequencing at an expected constant depth across the whole genome, it is possible to a priori select areas of the genome for sequencing (and so perform most of the sequencing in those areas). Exome sequencing targets sequencing of exons of genes by capturing short strands of DNA that overlap with those exons, and then sequencing the short strands of DNA. Exons are of high functionable and actionable interest. Directly sequencing exons allows for the observation of the genetic variation of a particular individual sample without reference to any other samples. Exome sequencing returns unbiased functionable and actionable genetic variation at a much reduced cost compared to whole genome sequencing though it only targets about 1% of the genome.

An alternative to sequencing strategies is to observe genetic variation using DNA microarray technology, which were developed at scale earlier than sequencing. DNA microarray technology enables a DNA-chip, for example, to assay hundreds of thousands of specific variants at one time. These genetic variants normally represent genetic variation across the whole genome. Genotyping arrays that measure genetic variation at 100,000s to 1,000,000s of variable sites in DNA are the workhorse of modern human genetics. The variable sites that are measured by each array are typically selected to represent common genetic variation in one or more populations of interest. The strategy provides an affordable and effective alternative to direct whole genome sequencing and is currently used to genotype millions of DNA samples every year. The resulting data enables consumer genetics companies to estimate individual ancestry and match individuals to their DNA relatives. It also powers the genome-wide association studies (GWAS), genomic risk score and Mendelian Randomization analyses that are providing many insights into the biology of diverse complex traits related to human health and behavior, ranging from cardiovascular and metabolic disease to psychiatric disorders and human behavior to aging related disorders and cancer.

Conventional strategies for array design focus on a set known common genetic variants and attempt to identify a subset of these variants that are expected to perform well in multiplex genotyping experiments and that also provide adequate representation of other known common variants. Typically, each variant is assigned a Probe score that measures its expected performance on an array platform. This score summarizes factors such as the presence of other nearby variants, repetitiveness, the proportion of guanine-cytosine (GC) bases in the probe DNA sequence, and the performance of similar probes in previous genotyping arrays. Each of these factors can affect the performance of genotyping probes targeting the variant. In addition to this Probe score, which summarizes the expected performance of the probe, variants are typically also mapped to a list of other common variants that they can represent. A variant that represents variation at other nearby common variants is "proxy" or "surrogate" for those additional variants. These proxy relationships are common among nearby variants in the human genome due to a process known as linkage disequilibrium. Linkage disequilibrium is the result of how genetic variants enter a population, through mutation or migration, and then gradually spread, through inheritance and recombination and gene conversion. Together, mutation, migration, inheritance, recombination, and gene conversion often cause nearby genetic variants to occur in predictable combinations, which typically reflect the ancestral chromosomes in which each variant first entered the population.

A genotyping array, such as a DNA microarray, only observes a small subset of the variants in an individual sample. Selecting a set of variants to include in a genotyping array, which variants are directly observed, ultimately involves selecting a set of directly observed variants with high "Probe scores" that can serve as "proxies" for a large portion of all known genetic variants. It is possible to indirectly observe (impute) variants from the directly observed variants. This process is called imputation. Imputation is successful because our genetic variation is inherited in such a way that the closer the variants are to each other on the same chromosome, the higher the probability that they were inherited from the same ancestor. Imputation methods take account of the approximations in the manner in which segments of DNA are inherited and have been shown to provide high quality results for imputing variants that are not directly observed. While this strategy results in lists of variants that provide good representation of common genetic variation in humans, it is also inefficient for technologies that measure multiple genetic variants with a single probe. Another problem with DNA microarray assays is that they are a completely separate process in the laboratory and require duplication of many processes, which leads to lab inefficiency. What is needed is a cost-effective lab strategy to enable direct sequencing of desired targeted regions while retaining the ability to impute variants across the whole genome.

Genotyping technologies have remained largely unchanged for almost two decades. Arrays produce high quality data and consistent results at low cost, but they are labor intensive. Arrays require additional processing and equipment, distinct from that used for whole exome sequencing. Arrays have limited scalability and customizability. There is a need for efficient processing of millions of samples.

SUMMARY

The present disclosure provides methods for manufacturing nucleic acid probes for genotyping by sequencing, the methods comprising: a) selecting a plurality of directly observed genetic variants to capture by the nucleic acid probes; b) eliminating low confidence variants from the plurality of directly observed genetic variants, thereby producing a filtered plurality of directly observed genetic variants; c) phasing the filtered plurality of directly observed genetic variants; d) identifying the presence or absence of one or more proxy variants for each variant within the filtered plurality of directly observed genetic variants; e) selecting a plurality of candidate regions of genomic DNA comprising the filtered plurality of directly observed genetic variants, wherein each candidate region of genomic DNA comprises from about 25 to about 150 bases, and comprises at least one variant among the filtered plurality of directly observed genetic variants; f) calculating a Quality score for each candidate region of genomic DNA that estimates the capture efficiency and alignment success of a probe; g) calculating a Probe score for each candidate region of genomic DNA by multiplying the Quality score by the number of variants captured by the candidate region of genomic DNA, wherein the number of variants captured by the candidate region of genomic DNA is the sum of the number of directly observed variants captured by the candidate region of genomic DNA and the number of corresponding proxy variants in different candidate regions of genomic DNA; h) selecting one or more candidate regions of genomic DNA having the highest Probe score for inclusion in a final set of regions of genomic DNA; i) repeating steps g) and h) on unselected candidate regions of genomic DNA for inclusion in the final set of regions of genomic DNA, wherein the number of variants in the unselected candidate region of genomic DNA is the sum of: 1) the number of directly observed variants in the unselected candidate region of genomic DNA excluding any directly observed variant within a previously selected region of genomic DNA, and 2) the number of corresponding proxy variants in different candidate regions of genomic DNA excluding any proxy variant corresponding to a directly observed variant within a previously selected region of genomic DNA, wherein steps g) and h) are repeated until a maximum number of regions of genomic DNA has been selected; and j) generating a set of nucleic acid probes complementary to the nucleic acid sequence of each of the genomic regions among the final set of regions of genomic DNA.

The present disclosure also provides methods for genotyping a DNA sample by sequencing, the methods comprising: a) hybridizing a set of nucleic acid probes manufactured as described above to the DNA sample to generate probe-hybridized genomic DNA; b) sequencing the probe-hybridized genomic DNA to produce a plurality of sequencing reads; c) mapping the plurality of sequencing reads to a reference genome; d) calling the directly observed variants present in the mapped sequencing reads; and e) imputing unobserved variants from unsequenced regions of genomic DNA, thereby establishing a genotype of the sample DNA.

The present disclosure also provides methods for genotyping a DNA sample by sequencing using a set of nucleic acid probes, the methods comprising: a) selecting a plurality of regions of genomic DNA from the DNA sample comprising a plurality of directly observed genetic variants; b) identifying the set of nucleic acid probes for hybridization to the selected plurality of regions of genomic DNA; c) hybridizing the set of nucleic acid probes to the DNA sample to generate probe-hybridized genomic DNA; d) sequencing the probe-hybridized genomic DNA to produce a plurality of sequencing reads; e) mapping the plurality of sequencing reads to a reference genome; f) calling the directly observed variants present in the mapped sequencing reads; and g) imputing unobserved variants from unsequenced regions of genomic DNA, thereby establishing a genotype of the sample DNA.

DESCRIPTION OF EMBODIMENTS

Figure 1:
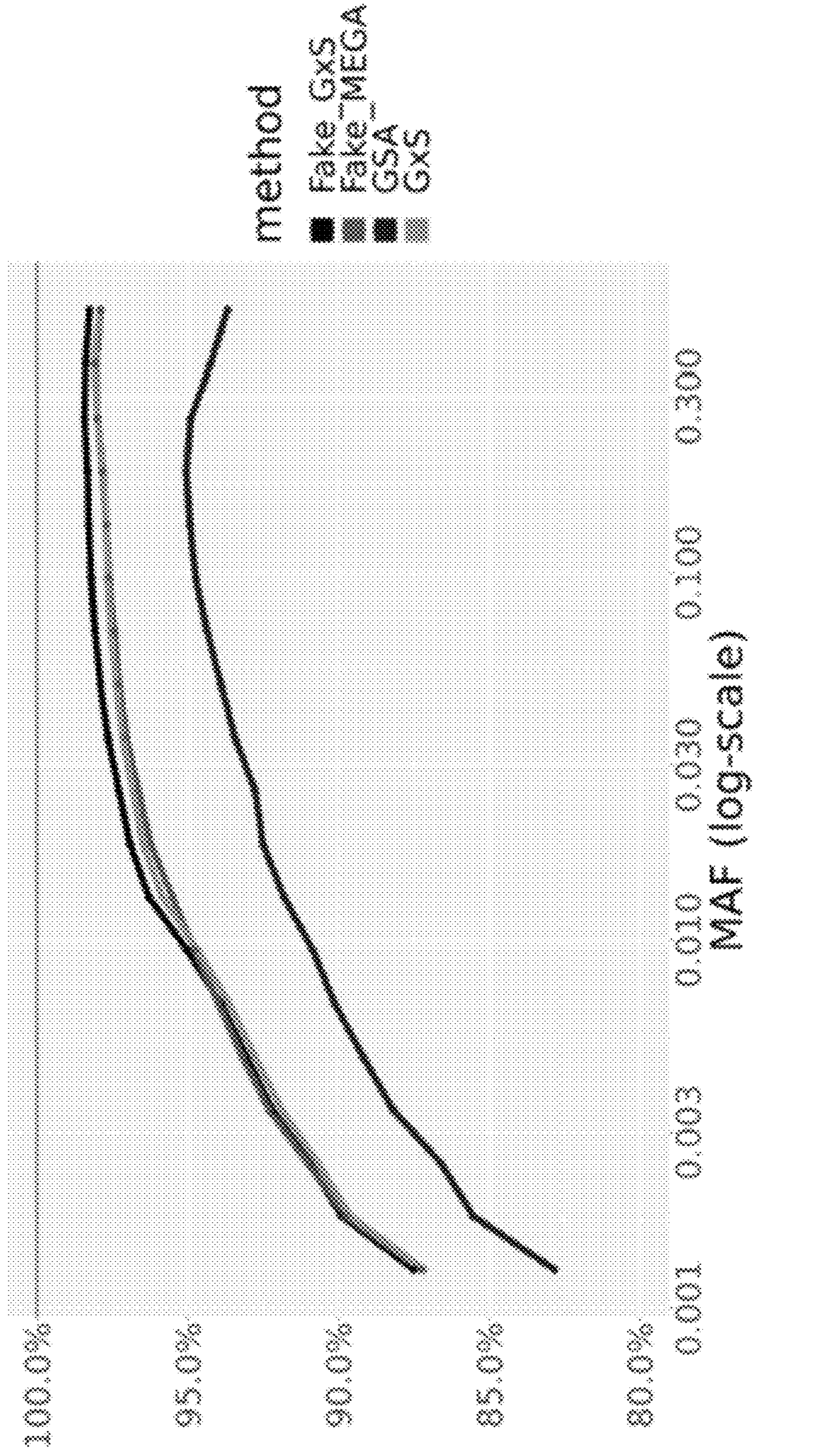
FIG. 1 shows imputation Rsq by variant bins for two different observations, one being the Global Screening Array (GSA), and the other being the Genotyping-by-Sequencing approach (GxS) described herein, and two in silico versions for comparison, one being denoted as "Fake_GxS", which has all the variants in the probes from the probe regions observed and the other being denoted as "Fake_MEGA", which has all the variants in regions assayed by the MEGA microarray (with 1.8 M variants).

Provided herein is a general strategy that can be used to efficiently design sets of nucleic acid probes, where each probe can target multiple genetic variants, for use in, for example, capture-based "genotyping by sequencing" methods. These capture-based "genotyping by sequencing" methods target short segments of the genome (the "target regions," each of which is typically 10 to 100s of base pairs in length) that can each include multiple known genetic variants. Selecting variants to target individually is inefficient for these experiments. For example, in a worst-case scenario, targeting 100,000 variants each selected independently, may require 100,000 short target regions. In more desirable scenarios, these 100,000 variants would be clustered together and may be captured with a much smaller number of probes. For example, more desirable methods identify a set of 100,000 variants that may be genotyped while capturing only 25,000 short target regions (if each target region includes an average of 4 variants) or 50,000 short target regions (if each target region includes an average of 2 variants). Alternately, the set of probes may identify 100,000 short target regions that capture 200,000 to 400,000 variants (and are, thus, likely to greatly outperform the 100,000 target regions that would be selected after selecting 100,000 variants independently).

The methods described herein identify a small set of genomic regions for sequencing that aim to approach the comprehensiveness of whole genome sequencing at a greatly reduced cost and effort. These regions are selected so that they are expected to perform well in targeted capture experiments. Further, when considered together, these regions contain a set of common genetic variants that accurately summarize variation in the genome for the purposes of GWAS, ancestry estimation, identification of genetic relatives, polygenic risk score estimation, and other applications that currently rely on genotyping arrays.

The methods described herein provide a sequencing-based alternative to genotyping arrays. The methods described herein provide better coverage of the genome than standard arrays, across multiple ancestries. A large number of common variants, such as about 1.4M, can be selected to enable highly accurate imputation across ancestries. The methods described herein can also cover about 4.5M to 5.0M common variants per sample with one sequencing read or greater. The reagents described herein have been iteratively refined by applying it to samples of diverse ancestries. Characteristics of the methods described herein include, but are not limited to, generation of data in tandem to whole exome sequencing of each sample, the bulk of the 1.4M common variants are selected to enable imputation of variation across the genome, and additional variants target known genome wide association study peaks, mitochondrial DNA, the Y chromosome, and the MHC. The methods described herein produce high-fidelity genotypes for about 1.4M variants per sample. These 1.4M variants have about 98.9% call rate and about 99.7% accuracy compared to deep whole genome sequencing data. These 1.4M variants can be used as stand-in replacements for array genotypes in most applications. The methods described herein are bioinformatically efficient, adding less than about 10 hours of CPU time to a typical exome processing procedure. Each sample can be processed and handled independently.

The sequencing-based approach for genotyping described herein is built on the high-throughput DNA capture technology described herein. The DNA capture methodology described herein is highly automated and scaled to process millions of samples per year. High quality exome data and genotyping can be executed simultaneously, facilitating integration of results. The methods described herein also have an advantage of being able to evolve over time and allow improved coverage of high-interest regions or variants. The methods described herein achieve differential sequence coverage and accuracy at high-value variants. The methods described herein both maximize tagging and minimizes the number of capture targets. The probe set described herein has been validated and improved by using it on a variety of samples and removing/replacing poor targets. Probes are selected to represent genetic variation across multiple ancestries and have been experimentally validated. The probe set targets about 1.5M variant sites per sample, and the sites targeted cover about 2.6% of the genome.

The terminology used herein is for the purpose of describing particular embodiments only and is not intended to be limiting.

The methods described herein provide for the selection and manufacture of a set of nucleic acid probes such that each probe can efficiently capture short strands of DNA that overlap with the probe and produce sequencing reads that can also be aligned. In addition, the methods described herein focus on regions of genomic DNA with genetic variation that enables either good imputation of the neighboring unobserved genetic variation (i.e., imputed variants) and/or the direct observation of a key variation.

The present disclosure provides methods for manufacturing nucleic acid probes for genotyping by sequencing, the methods comprising: a) selecting a plurality of directly observed genetic variants to capture by the nucleic acid probes; b) eliminating low confidence variants from the plurality of directly observed genetic variants, thereby producing a filtered plurality of directly observed genetic variants; c) phasing the filtered plurality of directly observed genetic variants; d) identifying the presence or absence of one or more proxy variants for each variant within the filtered plurality of directly observed genetic variants; e) selecting a plurality of candidate regions of genomic DNA comprising the filtered plurality of directly observed genetic variants, wherein each candidate region of genomic DNA comprises from about 25 to about 150 bases, and comprises at least one variant among the filtered plurality of directly observed genetic variants; f) calculating a Quality score for each candidate region of genomic DNA that estimates the capture efficiency and alignment success of a probe; g) calculating a Probe score for each candidate region of genomic DNA by multiplying the Quality score by the number of variants captured by the candidate region of genomic DNA, wherein the number of variants captured by the candidate region of genomic DNA is the sum of the number of directly observed variants captured by the candidate region of genomic DNA and the number of corresponding proxy variants in different candidate regions of genomic DNA; h) selecting one or more candidate regions of genomic DNA having the highest Probe score for inclusion in a final set of regions of genomic DNA; i) repeating steps g) and h) on unselected candidate regions of genomic DNA for inclusion in the final set of regions of genomic DNA, wherein the number of variants in the unselected candidate region of genomic DNA is the sum of: 1) the number of directly observed variants in the unselected candidate region of genomic DNA excluding any directly observed variant within a previously selected region of genomic DNA, and 2) the number of corresponding proxy variants in different candidate regions of genomic DNA excluding any proxy variant corresponding to a directly observed variant within a previously selected region of genomic DNA, wherein steps g) and h) are repeated until a maximum number of regions of genomic DNA has been selected; and j) generating a set of nucleic acid probes complementary to the nucleic acid sequence of each of the genomic regions among the final set of regions of genomic DNA.

The present disclosure also provides methods for designing nucleic acid probes for genotyping by sequencing, the methods comprising: a) selecting a plurality of directly observed genetic variants to capture by the nucleic acid probes; b) eliminating low confidence variants from the plurality of directly observed genetic variants, thereby producing a filtered plurality of directly observed genetic variants; c) phasing the filtered plurality of directly observed genetic variants; d) identifying the presence or absence of one or more proxy variants for each variant within the filtered plurality of directly observed genetic variants; e) selecting a plurality of candidate regions of genomic DNA comprising the filtered plurality of directly observed genetic variants, wherein each candidate region of genomic DNA comprises from about 25 to about 150 bases, and comprises at least one variant among the filtered plurality of directly observed genetic variants; f) calculating a Quality score for each candidate region of genomic DNA that estimates the capture efficiency and alignment success of a probe; g) calculating a Probe score for each candidate region of genomic DNA by multiplying the Quality score by the number of variants captured by the candidate region of genomic DNA, wherein the number of variants captured by the candidate region of genomic DNA is the sum of the number of directly observed variants captured by the candidate region of genomic DNA and the number of corresponding proxy variants in different candidate regions of genomic DNA; h) selecting one or more candidate regions of genomic DNA having the highest Probe score for inclusion in a final set of regions of genomic DNA; and i) repeating steps g) and h) on unselected candidate regions of genomic DNA for inclusion in the final set of regions of genomic DNA, wherein the number of variants in the unselected candidate region of genomic DNA is the sum of: 1) the number of directly observed variants in the unselected candidate region of genomic DNA excluding any directly observed variant within a previously selected region of genomic DNA, and 2) the number of corresponding proxy variants in different candidate regions of genomic DNA excluding any proxy variant corresponding to a directly observed variant within a previously selected region of genomic DNA, wherein steps g) and h) are repeated until a maximum number of regions of genomic DNA has been selected.

The methods comprise selecting a plurality of genetic variants to capture by the nucleic acid probes. These selected variants will constitute the desired set of "directly observed genetic variants." A "directly observed genetic variant" or a "directly observed variant" is a variant that is present in the genomic DNA that is captured by the hybridization of at least one probe, and which is subsequently sequenced. A directly observed variant is in contrast to the remaining genetic variants which will comprise the imputed variant. Any imputed variant is likely to also be in the same genomic DNA but is not captured by the hybridization of at least one probe and, thus, the imputed variant is not subsequently sequenced. The presence of the directly observed variants in the genomic DNA and subsequent sequencing thereof allows for the imputation of the imputed variants.

The plurality of directly observed genetic variants to capture by the nucleic acid probes can include any desired number of known common variants. For example, a set of M known genetic variants can be considered as $V_1$, $V_2$, $V_3 \ldots V_M$. The indexes m and n, which vary between 1 and M, be used to designate individual variants. Each variant $V_m$ has a known chromosomal position $P_m$ and set of alleles $A_m$ and each variant $V_n$ has a known chromosomal position $P_n$ and set of alleles $A_n$. In some embodiments, the plurality of directly observed genetic variants comprises every single known common variant. In some embodiments, the plurality of directly observed genetic variants is selected from a database of genome-wide associations of genetic variants, a database of pharmacogenetic associations of genetic variants, a database containing genetic variants within the whole mitochondrial chromosome, and/or a database of genetic variants in a microarray, or any combination thereof.

In some embodiments, the plurality of directly observed genetic variants is selected from one or more databases of genome-wide associations of genetic variants. Any database of genome-wide associations of genetic variants can be used for the identification of one or more directly observed genetic variants to include. In some embodiments, the database of genome-wide associations of genetic variants is a catalogue of known genome-wide association hits (see, for example, the world wide web at "ebi.ac.uk/gwas/"). In some embodiments, the sourced file was "gwas_catalog_v1.0.2-associations_e96_r2019-07-30.tsv." In some embodiments, not all variants in the database of genome-wide associations of genetic variants are selected. In some embodiments, a variant within the database of genome-wide associations of genetic variants is selected to be within the plurality of directly observed genetic variants when the association of the variant with a trait has a p-value$\leq 10^{-9}$. In some embodiments, a variant within the database of genome-wide associations of genetic variants is excluded from the plurality of directly observed genetic variants when the association with a trait has a p-value$>10^{-9}$. In some embodiments, this P-value analysis excludes variants present in the Y chromosome and mitochondria chromosome. In some embodiments, the number of variants selected from the database(s) of genome-wide associations of genetic variants is from about 30,000 to about 45,000. In some embodiments, the number of variants selected from the database(s) of genome-wide associations of genetic variants is from about 35,000 to about 40,000. In some embodiments, the number of variants selected from the database(s) of genome-wide associations of genetic variants is about 38,000. It is expected that the number of variants selected from the database(s) of genome-wide associations of genetic variants will change over time.

In some embodiments, the plurality of directly observed genetic variants is selected from one or more databases of pharmacogenetic associations of genetic variants. Any database of pharmacogenetic associations of genetic variants can be used for the identification of one or more directly observed genetic variants to include. In some embodiments, the database of pharmacogenetic associations of genetic variants is data released on pharmacogenetics associations by PharmGKB. In some embodiments, all sites observed as a single nucleotide polymorphism (SNP) that is in dbSNP and overlaps a gene of pharmacogenetic interest are included. In some embodiments, the number of variants selected from the database(s) of pharmacogenetic associations of genetic variants is from about 2,000 to about 10,000. In some embodiments, the number of variants selected from the database(s) of pharmacogenetic associations of genetic variants is from about 4,000 to about 6,000. In some embodiments, the number of variants selected from the database(s) of pharmacogenetic associations of genetic variants is about 5,000.

In some embodiments, the plurality of directly observed genetic variants is selected from one or more databases containing genetic variants within the whole mitochondrial chromosome. Any database containing genetic variants within the whole mitochondrial chromosome can be used for the identification of one or more directly observed genetic variants to include. In some embodiments, the whole mitochondria chromosome is tiled end-to-end.

In some embodiments, the plurality of directly observed genetic variants is selected from one or more databases of genetic variants in one or more microarrays. Any database of genetic variants in a microarray can be used for the identification of one or more directly observed genetic variants to include. An exemplary database is the variants on the microarray used by the UK Biobank. In some embodiments, the database of genetic variants in a microarray comprise genetic variants within: the HLA region of chromosome 6, the Y chromosome, the two killer cell immunoglobulin-like receptor (KIR) regions on chromosome 19, and the pseudo-autosomal regions 1 and 2 (Par1 and Par2) on the X chromosome.

In some embodiments, the database of genetic variants in a microarray comprises genetic variants within the HLA region of chromosome 6. In some embodiments, the database of genetic variants in a microarray comprises genetic variants within the HLA region of chromosome 6, defined as Chr6:28011410-33978119. Of course, equivalent coordinates in an alternate human genome assembly are included herein.

In some embodiments, the database of genetic variants in a microarray comprises genetic variants within the Y chromosome.

In some embodiments, the database of genetic variants in a microarray comprises genetic variants within the two KIR regions on chromosome 19. In some embodiments, the database of genetic variants in a microarray comprises genetic variants within the two KIR regions on chromosome 19, defined as Chr19:53961144-55367153 and Chr19:110783-760809. Of course, equivalent coordinates in an alternate human genome assembly are included herein.

In some embodiments, the database of genetic variants in a microarray comprises genetic variants within Par1 and Par2 on the X chromosome. In some embodiments, the database of genetic variants in a microarray comprises genetic variants within Par1 and Par2 on the X chromosome, defined as ChrX:10425-2774669 and ChrX:155704030-156003450. Of course, equivalent coordinates in an alternate human genome assembly are included herein. In some embodiments, the number of variants selected from the database(s) of genetic variants in a microarray is from about 700,000 to about 900,000. In some embodiments, the number of variants selected from the database(s) of genetic variants in a microarray is from about 800,000 to about 850,000. In some embodiments, the number of variants selected from the database(s) of genetic variants in a microarray is about 830,000.

In some embodiments, the multiallelic variants are converted to one or more sets of biallelic variants. There are two steps to the conversion, one step involves converting the variant in the abstract, and another step involves converting individual genotypes. In some embodiments, multi-allelic genotypes for the original multi-allelic variant are converted into bi-allelic genotypes for each of the decomposed genetic variants to allow estimation of linkage disequilibrium coefficients and proxy relationships between genetic variants. The methods described herein can accommodate multi-allelic variants by decomposing each of these into a series of bi-allelic variants that are all assigned the same chromosomal position but different alleles. For example, when a particular multiallelic variant has a single reference allele and three alternate alleles, the multiallelic variant is converted to three sets of biallelic variants (i.e., reference allele and first alternate allele, reference allele and second alternate allele, and reference allele and third alternate allele).

In some embodiments, to calculate metrics for possible imputation success, the whole genome sequencing dataset of the one thousand genomes project (denoted 1KG) was sourced. The high coverage (30x) sequencing of the 2,504 samples from 26 different populations was released for commercial use by the New York Genome Center in May 2019 (see, world wide web at "internationalgenome.org/data-portal/data-collection/30x-grch38").

The methods also comprise eliminating low confidence variants from the plurality of directly observed genetic variants, thereby producing a filtered plurality of directly observed genetic variants. Elimination of low confidence variants from the plurality of directly observed genetic variants serves as a quality control to limit the selected variants to variants in which there is high confidence. In some embodiments, eliminating low confidence variants from the plurality of potential directly observed genetic variants retains about 15 million variants. Elimination of low confidence variants from the plurality of directly observed genetic variants can include any one or more of the following:

In some embodiments, eliminating low confidence variants from the plurality of directly observed genetic variants comprises eliminating any variant that has a minor allele frequency (MAF) below a desired threshold value. For example, an allele frequency range can be considered as $f_{min}$ to $f_{max}$. The variants in V can be restricted to those variants that have minor allele frequency greater than or equal to $f_{min}$ and lesser than or equal to $f_{max}$. For example, $f_{max}$ can be 0.50. In addition, $f_{min}$ can be 1% (0.01) or 5% (0.05). In some embodiments, the desired threshold value is 1% (0.01). In some embodiments, this MAF threshold can be lowered to 0.1% (0.001).

In some embodiments, eliminating low confidence variants from the plurality of directly observed genetic variants comprises eliminating any variant that has a missingness greater than a desired threshold value. In some embodiments, the desired threshold value is 2%.

In some embodiments, eliminating low confidence variants from the plurality of directly observed genetic variants comprises removing variants that have a Hardy-Weinberg test of association with a P-value of $<10^{-8}$ within any of the sample populations.

The methods also comprise phasing the filtered plurality of potential directly observed genetic variants. In some embodiments, the methods comprise phasing all the variants observed in the 1000 Genome Samples or another reference panel. Phasing these variants helps the methods and algorithm for selecting "directly observed variants" and "probes" to perform better. Phasing produces a best estimate of the sequence of the variants on each of the two chromosomes per sample. Phasing variants in the 1000 Genomes Reference panel (or another panel of reference individuals) improves handling of any missing data and estimates of linkage disequilibrium and proxy relationships between variants. In contrast, genotyping only has the information of the count of particular alleles across the combination of both chromosomes. For example, a sequence of allele counts 0,1,2,2,1,1 may be phased as two binary sequences 0,1,1,1,1,1 and 0,0,1,1,0,0 which represent the two sequences on each chromosome. Phasing of genotype calls can be performed by commercially available software, such as SHAPEIT4 (see, world wide web at "odelaneau.github.io/shapeit4/") using all the normal defaults.

The methods also comprise identifying the presence or absence of one or more proxy variants for each directly observed variant within the filtered plurality of directly observed genetic variants. Each of the variants within the filtered plurality of directly observed genetic variants can potentially be a proxy for other variants (i.e., proxy variants) that will not be probed or sequenced (i.e., the proxy variants are imputed into the sample DNA genome based on the presence of the directly observed variants). These proxy relationships are common among nearby variants in the human genome due to linkage disequilibrium. For example, to describe proxy relationships between two variants, the matrix R with entries $R_{mn}$ describing the linkage disequilibrium relationship between variants $V_m$ and $V_n$ can be used. Any number of suitable measures of linkage disequilibrium between variants exist and can be used in the methods described herein. In some embodiments, a variant within the filtered plurality of directly observed genetic variants has a corresponding proxy variant in another region of genomic DNA when the directly observed genetic variant and the proxy variant are within 1 MB of each other, and where the linkage disequilibrium between the two variants has a squared correlation exceeding a desired threshold (t) using the $r^2$ measure of linkage disequilibrium. The tunable parameter t describes the minimum amount of linkage disequilibrium required before two variants can be considered as proxies for each other. In some embodiments, the linkage disequilibrium between the two variants has a squared correlation (t) of at least 0.2 using the $r^2$ measure of linkage disequilibrium. In some embodiments, the linkage disequilibrium between the two variants has a squared correlation (t) of at least 0.5 using the $r^2$ measure of linkage disequilibrium. In some embodiments, the linkage disequilibrium between the two variants has a squared correlation (t) of at least 0.8 using the $r^2$ measure of linkage disequilibrium. In some embodiments, the linkage disequilibrium between the two variants has a squared correlation (t) of at least 0.9 using the $r^2$ measure of linkage disequilibrium. In some embodiments, the linkage disequilibrium between the two variants has a squared correlation (t) of at least 1.0 using the $r^2$ measure of linkage disequilibrium. In some embodiments, proxy variant is present in another candidate region of genomic DNA compared to its directly observed variant counterpart. Thus, when the value of $R_{mn}>t$, the two variants $V_m$ and $V_n$ are proxies for each other.

Typically, the set of known genetic variants V and their linkage disequilibrium relationships R can be estimated through sequencing or genotyping of a small set of individuals. The quality of the regions selected for sequencing will improve as the number of individuals in this set increases. Furthermore, it is desirable that this set of individuals should be ancestrally diverse or, at least, that it matches the ancestry composition of the individuals who will studied using the selected target regions.

In some embodiments, identifying the presence or absence of one or more proxy variants for each directly observed variant can be carried out by software for linkage disequilibrium. One such example is emeraLD (see, world wide web at "github.com/statgen/emeraLD") using normal defaults. Such software can be used to generate lists of pairs of variants within 1 Mb of each other and having a squared correlation exceeding a desired threshold t.

The methods also comprise selecting a plurality of candidate regions of genomic DNA (i.e., targeted regions) to capture with the nucleic acid probes. A goal is to identify a set of K candidate regions of genomic DNA, $T=T_1, T_2, T_3, \ldots T_K$. The index k, which varies between 1 and K, can be used to designate an individual candidate region of genomic DNA. Each candidate region of genomic DNA $T_k$ has a start position Start($T_k$), an end position End($T_k$), and a corresponding Probe score Score($T_k$) that describes the expected performance of the candidate region of genomic DNA in a targeted experiment. The candidate regions of genomic DNA comprise the filtered plurality of directly observed genetic variants.

A tunable parameter L defines the maximum allowed length of each candidate region of genomic DNA, which is the distance in bases between the start position Start($T_k$) and the end position End($T_k$) of the candidate region of genomic DNA. Setting L=1 results in a strategy that is analogous to the pairwise tagging algorithms often used to design standard arrays. In contrast, L in the range of 25 to 150 can be used in the present methods described herein. In some embodiments, each candidate region of genomic DNA comprises from about 25 to about 150 bases, and comprises at least one variant among the filtered plurality of directly observed genetic variants. In some embodiments, each candidate region of genomic DNA comprises from about 35 to about 140 bases, and comprises at least one variant among the filtered plurality of directly observed genetic variants. In some embodiments, each candidate region of genomic DNA comprises from about 45 to about 130 bases, and comprises at least one variant among the filtered plurality of directly observed genetic variants. In some embodiments, each candidate region of genomic DNA comprises from about 55 to about 125 bases, and comprises at least one variant among the filtered plurality of directly observed genetic variants. In some embodiments, each candidate region of genomic DNA comprises from about 65 to about 125 bases, and comprises at least one variant among the filtered plurality of directly observed genetic variants. In some embodiments, each candidate region of genomic DNA comprises from about 75 to about 125 bases, and comprises at least one variant among the filtered plurality of directly observed genetic variants. In some embodiments, each candidate region of genomic DNA comprises from about 85 to about 125 bases, and comprises at least one variant among the filtered plurality of directly observed genetic variants. In some embodiments, each candidate region of genomic DNA comprises from about 95 to about 125 bases, and comprises at least one variant among the filtered plurality of directly observed genetic variants. In some embodiments, each candidate region of genomic DNA comprises from about 105 to about 125 bases, and comprises at least one variant among the filtered plurality of directly observed genetic variants. In some embodiments, each candidate region of genomic DNA comprises from about 120 to about 125 bases.

In some embodiments, the plurality of candidate regions of genomic DNA comprises from about 5 million to about 50 million variants. In some embodiments, the plurality of candidate regions of genomic DNA comprises from about 10 million to about 40 million variants. In some embodiments, the plurality of candidate regions of genomic DNA comprises from about 20 million to about 30 million variants.

In some embodiments, the totality of the plurality of candidate regions of genomic DNA comprises from about 1 million to about 100 million basepairs. In some embodiments, the totality of the plurality of candidate regions of genomic DNA comprises from about 5 million to about 75 million basepairs. In some embodiments, the totality of the plurality of candidate regions of genomic DNA comprises from about 10 million to about 50 million basepairs. In some embodiments, the totality of the plurality of candidate regions of genomic DNA comprises from about 20 million to about 40 million basepairs.

In some embodiments, the plurality of candidate regions of genomic DNA is divided into separate analysis groups. In some embodiments, the plurality of candidate regions of genomic DNA is divided into separate chromosome analysis groups.

In some embodiments, a plurality of candidate regions of genomic DNA comprise more than one directly observed variant among the filtered plurality of directly observed genetic variants. For example, a candidate region of genomic DNA that comprises 120 bases can comprise four directly observed variants (i.e., $V_1$, $V_2$, $V_3$, and $V_4$). In this scenario, each of the four directly observed variants are present within the region of DNA that is probed with the nucleic acid probe set. The 120 base candidate region of genomic DNA can begin at the position of the first variant (i.e., $V_1 \ldots V_2 \ldots V_3 \ldots V_4 \ldots$). The 120 base candidate region of genomic DNA can end at the position of the last variant (i.e., $\ldots V_1 \ldots V_2 \ldots V_3 \ldots V_4$). Alternately, the 120 base candidate region of genomic DNA can begin and end at positions other than the variant positions (i.e., $\ldots V_1 \ldots V_2 \ldots V_3 \ldots V_4 \ldots$). Numerous different candidate regions of genomic DNA that comprise 120 bases and comprise the directly observed variants can exits (i.e., by shifting the starting position of the candidate region). Thus, multiple different candidate regions of genomic DNA that comprise 120 bases can comprise the same directly observed variant(s).

The methods also comprise calculating a Quality score for each candidate region of genomic DNA that estimates the capture efficiency and alignment success of a probe that hybridizes thereto. The Quality score can be used to determine which probes (and corresponding candidate region of genomic DNA) should be avoided. As stated above, multiple different candidate regions of genomic DNA that comprise 120 bases can comprise the same directly observed variant(s), and therefore a Quality score is calculated for each of these candidate regions of genomic DNA that comprise the same directly observed variant(s). In addition, a Quality score is calculated for each of the other candidate regions of genomic DNA that comprise different directly observed variant(s). In some embodiments, calculating the Quality score comprises determining a component score for each of a mappability metric, an insertion-deletion metric, and a classification metric of the candidate region of genomic DNA. The Quality score aims to combine these three pieces of information so that probes that work well in capturing the appropriate strands of DNA and the subsequent sequenced reads can be mapped back, avoid regions with insertion-deletion polymorphism or variation and preferentially select regions that work well according to expected performance of probe hybridization to DNA, which can be estimated as a function of sequence composition and uniqueness. The Quality score for each candidate region of genomic DNA is the multiplication product of each of the component scores for that candidate region of genomic DNA. The end result is a Quality score between 0 and 1 that correlates with probability of probe success. If any of the component scores are zero, then the overall Quality score will also be zero.

In some embodiments, the mappability metric (or multi-read mappability metric) is the probability that a randomly selected read of length kin a given region is uniquely mappable. In some embodiments, the mappability metric is the UMAP metric. In some embodiments, the component score for the mappability metric is the exponential of 10 times the multi-read mappability metric (denoted as $UmapMRM_i$ for position i). In some embodiments, the component score for the mappability metric is $\exp(10\times UmapMRM_i-9)$, wherein $UmapMRM_i$ is the multi-read mappability metric for the variant position i within the candidate region of genomic DNA. In some embodiments, the UMAP mapping metric, particularly the 100 bp multi-read mappability metric, has been pre-calculated across the genome and summarized in tables that are available for download (see, world wide web at “bismap.hoffmanlab.org/”).

In some embodiments, the insertion-deletion metric is a measure of the presence or absence of an insertion or deletion of bases (e.g., insertion-deletion polymorphisms or variations) within the candidate region of genomic DNA. Insertion-deletion is included as if the position i is connected to insertion-deletion variation, then the position is down-weighted. In some embodiments, the insertion-deletion variation component score is exp (SV $score_i$). In some embodiments, the SV $score_i$ is 2 when the variant position i is not connected to a insertion-deletion variation or connected to a insertion-deletion variation less than 5 bases. In some embodiments, the SV $score_i$ is 1 when the variant position i is connected to an insertion-deletion variation equal to or greater than 5 bases and less than or equal to 10 bases (e.g., a medium-sized insertion-deletion variant). In some embodiments, the SV $score_i$ is 0 when the variant position i is connected to an insertion-deletion variation greater than 10 bases (e.g., a large-sized insertion-deletion). In some embodiments, the SV $score_i$ is 2 when the variant position is not near an insertion-deletion variant, the SV $score_i$ is 1 when the variant position is near an insertion-deletion variant of ≥5 and <10 bases, and the SV $score_i$ is 0 when the variant position is near an insertion-deletion variant of ≥10 bases. A tunable parameter can define the maximum length of insertion-deletion polymorphisms that fall within a candidate region of genomic DNA. This tunable parameter can depend on the tolerance for mismatch between probes used for targeting and the sequences that are present in each sample being studied.

In some embodiments, the classification metric of the candidate region of genomic DNA comprises a first category (e.g., the worst performing category), a second category (e.g., a bad performing category), a third category (e.g., a poor performing category), and a fourth category (e.g., a good performing category). The order of best performance to worst performance is: fourth category, third category, second category, and first category. In some embodiments, a first component score for the classification metric is a score by position, which is exp(Region_$score_i$), whereby a variant position i in the first category is scored as a 0, a variant position i in the second category is scored as a 1, a variant position i in the third category is scored as a 1.6, and a variant position i in the fourth category is scored as a 2. In some embodiments, a second component score, which is a minimum absolute distance score, for the classification metric is:

$$\left(1+1.2\left(\frac{\min(dist2category1_i,\ 60)}{60}\right)\right)$$

wherein $dist2category1_i$ is the minimum absolute distance from the variant position i to a region in the first category. In some embodiments, a third component score for the classification metric is:

$$\left(1+1.2\left(\frac{\min(dist2category2_i,\ 60)}{60}\right)\right)$$

wherein $dist2category2_i$ is the minimum absolute distance from the variant position i to a region in the second category. These two component scores down-weight probes that are not in category 1 or category 2 (i.e., bad or worst regions) but are very close, so that reads produced from the probe might have bad alignment.

In some embodiments, a trait to be used to place a particular candidate region of genomic DNA in a particular category can be the % GC content with a corresponding complementary probe/primer. For example, the % GC content of probes/primers is desirable to be from about 40% to about 55%. Thus, in some embodiments, the first category may have corresponding probes/primers with a % GC content less than about 40%; the second category may have corresponding probes/primers with a % GC content greater than 55%; the third category may have corresponding probes/primers with a % GC content of about 50% to about 55%; and the fourth category may have corresponding probes/primers with a % GC content of from about 40% to about 55%. Additional traits that can be used to categorize particular candidate regions of genomic DNA include, but are not limited to, primer/probe melting temperature, primer/probe annealing temperature, the presence or absence of a GC clamp, 3' end stability, and the like. Each of these traits can be split into four categories based upon the user’s desired preference.

The overall Quality score is the multiplication product of the 5 component scores. In some embodiments, the Quality score for each candidate region of genomic DNA is scaled to be between 0 and 1 by dividing by the maximum score (which is $\exp(5)\times1.2^2$; or approximately 213.7149), thereby producing a Quality score for each candidate region of genomic DNA.

In regard to the overall Quality score, a decision made about which probe to select for any particular candidate region of genomic DNA can be relative. Thus, regional characteristics (such as GC content) that lower the scores for many neighboring probes do not necessarily exclude the region from consideration. Instead, our method will attempt to select the best available probes in such regions. In addition, the Quality score can also contain a metric favoring probes that are evenly distributed across the genome.

The methods also comprise calculating a Probe score for each candidate region of genomic DNA. In some embodiments, the Probe score is calculated by multiplying the Quality score by the number of variants captured by the candidate region of genomic DNA. For instance, each candidate region of genomic DNA $T_k$ can overlap a set of genetic variants, which can be termed OverlapSet($T_k$), which includes all genetic variants whose positions fall between Start($T_k$) and End($T_k$). In addition to the variants it overlaps directly, each candidate region of genomic DNA $T_k$ will also capture variants that have a proxy in OverlapSet ($T_k$). This set can be termed the proxy set for region $T_k$, which can be termed ProxySet($T_k$), and which includes all variants in the OverlapSet($T_k$) as well as all other variants m for which there exists a corresponding variant n within the OverlapSet($T_k$) such that $R_{mn}>t$. Thus, in some embodiments, the number of variants captured by the candidate region of genomic DNA is the sum of the number of directly observed variants captured by the candidate region of genomic DNA (i.e., within the candidate region that is to be hybridized to the probes) and the number of corresponding proxy variants in different candidate regions of genomic DNA.

For example, assuming a particular candidate region of genomic DNA comprises three directly observed variants (i.e., $V_1$, $V_2$, and $V_3$), and $V_1$ has two corresponding proxy variants $PV_a$ and $PV_b$ in different candidate regions of genomic DNA, $V_2$ has four corresponding proxy variants $PV_c$, $PV_d$, $PV_e$, and $PV_f$ in different candidate regions of genomic DNA, and $V_3$ has five corresponding proxy variants $PV_g$, $PV_h$, $PV_i$, $PV_j$, and $PV_k$ in different candidate regions of genomic DNA, then the number of directly observed variants captured by the candidate region of genomic DNA is three (i.e., $V_1$, $V_2$, and $V_3$) and the number of corresponding proxy variants in different candidate regions of genomic DNA is 11 (i.e., $PV_a$, $PV_b$, $PV_c$, $PV_d$, $PV_e$, $PV_f$, $PV_g$, $PV_h$, $PV_i$, $PV_j$, and $PV_k$). Thus, the sum of the number of directly observed variants captured by the candidate region of genomic DNA and the number of corresponding proxy variants in different candidate regions of genomic DNA is 14. Accordingly, the Probe score for this particular candidate region of genomic DNA is the multiplication product of the Quality score and 14.

The methods also comprise selecting one or more candidate regions of genomic DNA having the highest Probe score for inclusion in a final set of regions of genomic DNA. In some embodiments, a single candidate region of genomic DNA having the highest Probe score is selected for inclusion in a final set of regions of genomic DNA. In some embodiments, more than one candidate region of genomic DNA having the highest Probe score is selected for inclusion in a final set of regions of genomic DNA. In some embodiments, when multiple candidate regions of genomic DNA with the highest Probe score exist, candidate region(s) of genomic DNA that are more evenly spaced throughout the genome are selected.

In selecting a set of candidate regions of genomic DNA to measure experimentally, a goal is to minimize the number of regions in T, maximize the overall quality of these regions, as summarized by their overall Probe scores Score($T_k$), and to maximize the number variants captured in the union of ProxySet($T_k$) for candidate regions of genomic DNA. When multiple similarly performing sets of candidate regions of genomic DNA exist, sets of candidate regions of genomic DNA that are evenly spaced throughout the genome can be favored because these evenly spaced sets of candidate regions of genomic DNA appear to outperform alternatives in practice.

As stated herein, a step in the methods described herein is the identification of a set of candidate regions of genomic DNA to be evaluated. Since the human genome is approximately 3 billion base pairs long, there are, potentially, on the order of $3\times10^9$ potentially candidate regions of genomic DNA of length L (when L is small relative to genome size). The number of candidate variants to be potentially selected is much smaller, typically on the order of 5 to 50 million variants (depending on the allele frequency range of variants). The list of candidate regions of genomic DNA is seeded with a suggested candidate region of genomic DNA for each variant. This suggested candidate regions of genomic DNA will include the variant and all variants that are within L base pairs to its right. Among all possible candidate regions of genomic DNA that meet this criterion, a focus is on the suggested candidate region of genomic DNA that has the highest Probe score, Score($T_k$). An improvement in performance is possible by also considering regions that include only a subset of the variants that are L base pairs to the right but that have higher region Probe scores. For example, where variant $V_m$ and three additional variants $V_{m+1}$, $V_{m+2}$, and $V_{m+3}$ are all within L base pairs to its right. Without loss of generality, the three variants can be sorted left to right according to their coordinates. The candidate region that includes $V_m$, $V_{m+1}$, $V_{m+2}$, and $V_{m+3}$ and has the highest possible score can be identified. The highest scoring candidate regions that include only $V_m$, $V_{m+1}$, and $V_{m+2}$ or only $V_m$ and $V_{m+1}$ can also be identified. These additional regions are only added to the list of potential candidate regions of genomic DNA if their Probe scores are higher than that for the best scoring region that includes $V_m$, $V_{m+1}$, $V_{m+2}$, and $V_{m+3}$. If these additional regions have lower region Probe scores, they would never be picked and can be safely ignored because the list of variants for which they serve as proxies will always be smaller or equal to the list of regions for which the higher scoring region can proxy. This optional step reduces the number of candidate regions of genomic DNA that must be considered in each iteration from billions to millions, resulting in substantial savings of computational time.

In some embodiments, an additional tunable parameter can be used to define the maximum number of variants allowed per candidate region of genomic DNA. In some embodiments, a candidate region of genomic DNA is omitted from the final set of regions of genomic DNA when the candidate region of genomic DNA would comprise more directly observed variants than a desired threshold value. In some embodiments, the desired threshold value is 5 directly observed variants.

The methods also comprise repeating steps g) (i.e., calculating a Probe score for each candidate region of genomic DNA) and h) (i.e., selecting one or more candidate regions of genomic DNA having the highest Probe score for inclusion in a final set of regions of genomic DNA) on unselected candidate regions of genomic DNA for inclusion in the final set of regions of genomic DNA. Thus, to identify a set of candidate regions of genomic DNA, the methods described herein proceed iteratively through a series of steps. In each iteration, one or more candidate regions of genomic DNA are selected for inclusion within the final set of candidate regions of genomic DNA, and the scores for other candidate regions of genomic DNA are updated. Selection of candidate region of genomic DNA for inclusion in the final set of candidate region of genomic DNA continues until a maximum number of candidate regions of genomic DNA has been selected or all variants of interest are either within a selected candidate region of genomic DNA or have a proxy within a selected candidate region of genomic DNA.

For example, after the first selection of the single or multiple candidate regions of genomic DNA described in the previous step, the remaining candidate regions of genomic DNA that have not yet been selected are now available for re-calculating Probe scores and selection for inclusion in a final set of regions of genomic DNA. For such repeating steps, the number of variants in any particular unselected candidate region of genomic DNA is the sum of: 1) the number of directly observed variants in the unselected candidate region of genomic DNA, but excluding any directly observed variant within a previously selected candidate region of genomic DNA, and 2) the number of corresponding proxy variants in different candidate regions of genomic DNA, but excluding any proxy variant corresponding to a directly observed variant within a previously selected candidate region of genomic DNA.

For example, assume a previously selected candidate region of genomic DNA (i.e., Candidate Region 1 from step h)) comprises two directly observed variants (i.e., $V_1$ and $V_2$). Also assume that $V_1$ has two corresponding proxy variants $PV_a$ and $PV_b$ in different candidate regions of genomic DNA, and $V_2$ has two corresponding proxy variants $PV_c$ and $PV_d$ in different candidate regions of genomic DNA. Also assume Candidate Region 2, which is under consideration for selection, comprises two directly observed variants (i.e., $V_2$ and $V_3$), where $V_2$ has two corresponding proxy variants $PV_c$ and $PV_d$ in different candidate regions of genomic DNA, and $V_3$ has two corresponding proxy variants $PV_e$ and $PV_f$ in different candidate regions of genomic DNA. When Candidate Region 2 is under consideration for selection, the number of directly observed variants in the unselected Candidate Region 2 excludes any directly observed variant within a previously selected candidate region of genomic DNA (i.e., $V_2$ from Candidate Region 1), and the number of corresponding proxy variants in different candidate regions of genomic DNA excludes any proxy variants corresponding to directly observed variants within a previously selected candidate region of genomic DNA (i.e., proxy variants $PV_c$ and $PV_d$ associated with $V_2$ from Candidate Region 1). Thus, in the scenario described herein, although Candidate Region 2 comprises two directly observed variants (i.e., $V_2$ and $V_3$), only one of them (i.e., $V_3$) is counted towards the number of number of directly observed variants for determining a Probe score. In addition, although Candidate Region 2 comprises four proxy variants (i.e., $PV_c$, $PV_d$, $PV_e$, and $PV_f$), only two of them (i.e., $PV_e$ and $PV_f$) are counted towards the number of number of corresponding proxy variants for determining a Probe score. Thus, in the present scenario, instead of having a Probe score for Candidate Region 2 that is the multiplication product of the Quality score for Candidate Region 2 and 6 (i.e., the sum of the two directly observed variants and the four corresponding proxy variants), the Probe score for Candidate Region 2 is the multiplication product of the Quality score for Candidate Region 2 and 3 (i.e., the sum of the single directly observed variant and the two corresponding proxy variants not yet present in any previously selected candidate region of DNA).

In some embodiments, after steps g) (i.e., calculating a Probe score for each candidate region of genomic DNA) and h) (i.e., selecting one or more candidate regions of genomic DNA having the highest Probe score for inclusion in a final set of regions of genomic DNA) are repeated, the Probe scores for the remaining unselected candidate regions of genomic DNA are updated.

In some embodiments, the update comprises, after selecting a candidate region of genomic DNA to include in the final set of regions of genomic DNA, re-calculating the Probe score of all remaining unselected candidate regions of genomic DNA that contain a proxy of a directly observed variant that was present in a previously selected candidate region of genomic DNA. In some embodiments, the update comprises eliminating all unselected candidate regions of genomic DNA that only contain directly observed variants and/or corresponding proxy variants that have already been selected for inclusion within the final set of regions of genomic DNA in a previous round of selection. In some embodiments, the update comprises both of the aforementioned updates.

In some embodiments, steps g) and h) are repeated until a maximum number of regions of genomic DNA has been selected. In some embodiments, steps g) and h) are repeated until all directly observed variants and proxy variants are contained within the final set of regions of genomic DNA.

All potential candidate regions of genomic DNA are cycled through each iteration. The incremental value of each region $T_k$ as the product of its Probe score Score($T_k$) and the number of variants in its proxy set ProxySet($T_k$) that are not in the proxy sets of previously selected regions are measured. A goal is to identify the candidate region of genomic DNA with the highest incremental value and to select it. When there are ties, the distance between the tied candidate regions of genomic DNA with maximal products and all previously selected candidate regions of genomic DNA and the tie is broken by selecting the candidate region of genomic DNA that is most distant from previously selected candidate regions of genomic DNA. This tie breaking strategy promotes even spacing of selected candidate regions of genomic DNA throughout the genome and improves performance of the methodology when analysis of the resulting candidate regions of genomic DNA and data is combined with modern haplotyping and imputation methodology.

After selecting the candidate regions of genomic DNA with highest incremental value and breaking any ties, if necessary, information for remaining candidate regions of genomic DNA can be updated. For example, two optional updates can be considered. First, the number of variants in the proxy set for each candidate region of genomic DNA that are not in the proxy sets of previously selected candidate regions of genomic DNA can be cached. This caching is not required, but greatly improves computational efficiency. When caching is enabled, after selecting a particular candidate region of genomic DNA $T_k$, all regions whose proxy sets overlap with ProxySet($T_k$) can be visited and updating the cached count of the number of variants in their proxy sets that are not in previously selected candidate regions of genomic DNA to reflect that some of the variants in their proxy sets are now captured through the selected candidate region of genomic DNA $T_k$. Second, if the Probe scores for each candidate region of genomic DNA depend on the Probe scores of other selected candidate regions of genomic DNA (for example, because the targeting technology being used does not allow for overlapping regions or because it must account for sequence complementarity between candidate regions of genomic DNA being targeted), the Probe scores of other candidate regions of genomic DNA can be updated to reflect the fact that candidate region of genomic DNA $T_k$ has been selected.

Before starting the next iteration, all candidate regions of genomic DNA whose proxy sets are empty or are fully contained within the union of proxy sets for currently selected candidate regions of genomic DNA can be removed from the list of candidate regions of genomic DNA to be evaluated. If caching is implemented, these regions will have cache scores of zero. These regions may never be picked because they do not improve the design and they can be safely removed from the list of candidate regions of genomic DNA to evaluate, to improve computational efficiency and increase the speed of future iterations. In addition, candidate regions of genomic DNA that have a cache score of 1 (that is, that capture only a single incremental variant) and where the captured variant is not captured by any other candidate regions of genomic DNA can be safely set aside for assessment in a final custom iteration. The methodology can proceed iteratively, selecting one candidate region of genomic DNA at a time, until all variants are in the proxy set of one the candidate regions of genomic DNA selected for targeting, or until the maximum number of candidate regions of genomic DNA has been targeted.

The methods described herein can be incorporated into an algorithm. Additional information can also be used to increase the computational efficiency of algorithms. For example, a challenging aspect of such an algorithm can be the storage of the matrix R. When the number of variants M being considered is large, the number of entries in this matrix, which is proportional to M×M, is extremely large and can exceed the capacity of random access memory (RAM) for most modern computers. In such situations, a sparse representation can be used for the matrix, with only entries whose values exceed the user defined threshold t that establishes proxy relationships loaded into RAM. In typical human data, large linkage disequilibrium coefficients are confined to a small number of variant pairs, and this sparse representation of the matrix can be easily stored in memory and used in the required computations.

In addition, although an algorithm can be efficient enough to be directly applied to the entire genome, a few efficiencies can be gained and can be considered, particularly in situations where selecting a candidate region of genomic DNA for targeting does not affect the Probe scores of other distant candidate regions of genomic DNA being considered. One of these efficiencies is to divide the genome into a series of regions where candidate regions of genomic DNA can be selected independently. In the simplest case, these regions can be individual chromosomes. In more refined cases, the entire genome can be partitioned into a series of non-overlapping regions such that $R_{mn}$ is guaranteed to be <t when m and n index variants in different regions. This partitioning can be carried out using standard algorithms to identify connected components within graphs. Partitioning improves computational efficiency, and allows for the algorithm to consider pairs, triples or other small tuples of candidate regions of genomic DNA in each iteration, instead of one candidate region of genomic DNA per iteration.

The iterative algorithm can provide a very high-quality solution that accounts for known linkage disequilibrium relationships, favors groups of clustered variants which can be targeted together because they fall in contiguous windows of L base pairs or less, allows for Probe scores for candidate regions of genomic DNA, and distributes probes evenly across the genome—it can accomplish all this in a computationally efficient manner. When the number of candidate regions of genomic DNA is modest (or when the algorithm to divide the genome into blocks that can be considered independently is used), it is possible to exhaustively enumerate and evaluate all possible combinations of candidate regions of genomic DNA. In this case, a global scoring scheme can be used to select the optimal combination of candidate regions of genomic DNA among all enumerated possibilities. To do this, the global scoring scheme can summarize the number of variants with a proxy within candidate regions of genomic DNA, the overall Probe scores of candidate regions of genomic DNA, and the even spacing of candidate regions of genomic DNA. Given a set of candidate regions of genomic DNA T, many suitable scoring schemes can be devised. Each variant of interest can be assigned the Probe score of the highest scoring candidate regions of genomic DNA among the selected candidate regions of genomic DNA that include the variant in their proxy sets. Variants that are not included in any proxy set can be assigned a score of zero. Then, the overall global score for each configuration can be a weighted sum of these assigned per variant scores (summed across all variants), a measure of the evenness of spacing of candidate regions of genomic DNA, such as the kurtosis of distribution of distances between consecutive selected probes, and a penalty to favor configurations with a smaller number of targets. This global scoring scheme can also be used together with simulated annealing or another Monte Carlo algorithm to allow refinement of an iterative solution suggested by the algorithm. This refinement can be possible even in situations where the set of all possible combinations of candidate regions of genomic DNA is too large to enumerate. As with other Monte Carlo schemes, simulated annealing explores solutions in the neighborhood of the current solution and requires a proposal scheme for suggesting new solutions in the neighborhood of the current solution (for example, by adding, removing, or replacing a candidate region of genomic DNA in the currently selected set), a scheme for accepting or rejecting proposed updates in a stochastic manner (for example, by always accepting solutions that improve the global score and sometimes accepting solutions that decrease the global score, to avoid becoming stuck in local minima), and a scheme for managing the stochastic component of the process so it becomes gradually more stringent and deciding when convergence has been achieved.

The methods also optionally comprise generating a set of nucleic acid probes. Each of the individual probes within the set of nucleic acid probes is complementary to the nucleic acid sequence of a genomic region among the final selected set of regions of genomic DNA. Thus, the totality of the set of nucleic acid probes is complementary to the totality of the nucleotide sequences of the final selected set of regions of genomic DNA. In some embodiments, the set of nucleic acid probes comprises from about 200,000 to about 700,000 probes. In some embodiments, the set of nucleic acid probes comprises from about 200,000 to about 600,000 probes. In some embodiments, the set of nucleic acid probes comprises from about 200,000 to about 500,000 probes. In some embodiments, the set of nucleic acid probes comprises from about 200,000 to about 400,000 probes. In some embodiments, the set of nucleic acid probes comprises from about 500,000 to about 700,000 probes. In some embodiments, the set of nucleic acid probes comprises from about 600,000 to about 650,000 probes. In some embodiments, each of the individual probes within the set of nucleic acid probes comprises from about 25 to about 150 bases, and is hybridizable to a particular candidate region of genomic DNA that comprises at least one directly observed variant. In some embodiments, each of the individual probes within the set of nucleic acid probes comprises from about 120 to about 125 bases. In some embodiments, one or more individual probes within the set of nucleic acid probes comprises the same number of bases as the corresponding candidate region of genomic DNA to which it is designed to hybridize. In some embodiments, one or more individual probes within the set of nucleic acid probes comprises a greater number of bases as the corresponding candidate region of genomic DNA to which it is designed to hybridize.

The present disclosure also provides methods for genotyping a DNA sample by sequencing, the methods comprising: a) hybridizing a set of nucleic acid probes manufactured as described herein to the DNA sample to generate probe-hybridized genomic DNA; b) sequencing the probe-hybridized genomic DNA to produce a plurality of sequencing reads; c) mapping the plurality of sequencing reads to a reference genome; d) calling the directly observed variants present in the mapped sequencing reads; and e) imputing unobserved variants from unsequenced regions of genomic DNA, thereby establishing a genotype of the sample DNA.

The DNA sample can be any DNA sample that is a source of DNA for genotyping. In some embodiments, the DNA sample is obtained from a subject having a disease or condition. In some embodiments, the DNA sample is obtained from a tumor from a subject.

The methods comprise hybridizing a set of nucleic acid probes manufactured as described herein to a DNA sample to generate probe-hybridized genomic DNA. The set of nucleic acid probes is contacted to the DNA sample under typical conditions for hybridization to occur. In some embodiments, when the average probe produces a coverage of X, probes having a coverage of <0.33X can be removed. Thus, for example, any probes that result in less than 8X coverage (when the average probe has a coverage of 24X) of the directly observed variants within the plurality of sequencing reads are removed from the set of nucleic acid probes. In some embodiments, any probes resulting in inefficient capturing of the sample DNA are removed from the set of nucleic acid probes. In some embodiments, probes that produce low average coverage but that target high-value variants (because they map to known functional regions of the genome or because they serve as proxies for many other variants), can be supplemented with additional copies in the capture reagent, instead of dropped. This supplementation can help improve the coverage they provide and facilitate accurate genotyping.

The methods also comprise sequencing the probe-hybridized genomic DNA to produce a plurality of sequencing reads. In some embodiments, the plurality of sequencing reads comprises about 30 million sequencing reads. In some embodiments, the plurality of sequencing reads comprises about 25 million sequencing reads. In some embodiments, the plurality of sequencing reads comprises about 20 million sequencing reads. In some embodiments, the plurality of sequencing reads comprises about 15 million sequencing reads. In some embodiments, the plurality of sequencing reads comprises about 10 million sequencing reads. In some embodiments, the plurality of sequencing reads comprises about 5 million sequencing reads. In some embodiments, the plurality of sequencing reads comprises about 1 million sequencing reads.

The methods also comprise mapping the plurality of sequencing reads to a reference genome.

The methods also comprise calling the directly observed variants present in the mapped sequencing reads. In some embodiments, low confidence called variants resulting from low coverage reads are eliminated to produce a final set of called directly observed variants. In some embodiments, low confidence called variants resulting from coverage reads less than 8X are eliminated. In some embodiments, eliminating low confidence called variants comprises imputing the same called directly observed variants from a reference panel of variants.

In some embodiments, the methods further comprise phasing the called directly observed variants into sets of known haplotypes. Examples of phasing can be found in, for example, U.S. Patent Application Publication No. 2019/0205502.

In some embodiments, the software GLIMPSE (see, world wide web at "odelaneau.github.io/GLIMPSE/"), or software providing the same functionality, can be used return refined variant calls after including information from neighboring variants. GLIMPSE enables the uncertainty in the variant calls from low coverage reads to be much reduced given the neighboring variant calls for each sample. A second step for GLIMPSE is to take those refined variant calls and phase the genotypes calls into variant calls per chromosome. GLIMPSE can be run using default parameters.

In some embodiments, the percentage of called variants having greater than 10X coverage is determined. In such embodiments, when the percentage of called variants having greater than 10X coverage is less than about 95%, the set of nucleic acid probes is re-hybridized to the DNA sample. This embodiment serves as an internal control for the hybridization and sequencing steps described herein.

In some embodiments, when called directly observed variants are close to or within regions of genomic DNA hybridizable to probes that have been eliminated from the set of nucleic acid probes, such directly observed variants are omitted from the final set of called directly observed variants.

The methods also comprise imputing unobserved variants from unsequenced regions of genomic DNA, thereby establishing a genotype of the sample DNA. In some embodiments, the unobserved variants are imputed from a reference panel of variants based on the presence of called directly observed variants in the DNA sample.

In some embodiments, the software Minimac3 (see, world wide web at "genome.sph.umich.edu/wiki/Minimac3") can be used for variant imputation (for unobserved and unsequenced variants) from the variant calls on each haplotype. Minimac3 can be performed using default parameters.

The present disclosure also provides methods for genotyping a DNA sample by sequencing using a set of nucleic acid probes, the methods comprising: a) selecting a plurality of regions of genomic DNA from the DNA sample comprising a plurality of directly observed genetic variants; b) identifying the set of nucleic acid probes for hybridization to the selected plurality of regions of genomic DNA; c) hybridizing the set of nucleic acid probes to the DNA sample to generate probe-hybridized genomic DNA; d) sequencing the probe-hybridized genomic DNA to produce a plurality of sequencing reads; e) mapping the plurality of sequencing reads to a reference genome; f) calling the directly observed variants present in the mapped sequencing reads; and g) imputing unobserved variants from unsequenced regions of genomic DNA, thereby establishing a genotype of the sample DNA. Steps a) through g) can be carried out according to the disclosure herein.

The present disclosure also provides systems and computer-readable media for carrying out the methods described herein.

In some embodiments, a computer program product is provided, comprising a computer-readable medium comprising instructions encoded thereon for carrying out any of the methods described herein. In some embodiments, the computer program product enables a computer having a processor to carry out any of the methods described herein. In some embodiments, the computer program product is encoded such that the program, when implemented by a suitable computer or system, can receive all parameters necessary to carry out any of the methods described herein. In some embodiments, a computer system for carrying out any of the methods described herein is provided, wherein the system comprises a processor and memory coupled to the processor, and wherein the memory encodes one or more computer programs that causes the processor to carry out any of the methods described herein.

The computer software product may be written using any suitable programming language known in the art. System components may include any suitable hardware known in the art. Suitable programming language and suitable hardware system components, include those described in the following U.S. Pat. No. 7,197,400 (see, e.g., cols. 8-9), U.S. Pat. No. 6,691,042 (see, e.g., cols. 12-25); U.S. Pat. No. 8,245,517 (see, e.g., cols. 16-17); U.S. Pat. No. 7,272,584 (see, e.g., col. 4, line 26-col. 5, line 18); U.S. Pat. No. 8,203,987 (see, e.g., cols. 19-20); U.S. Pat. No. 7,386,523 (see, e.g., col. 2, line 26-col. 3, line 3; see also, col. 8, line 21-col. 9, line 52); U.S. Pat. No. 7,353,116 (see, e.g., col. 5, line 50-col. 8, line 5), U.S. Pat. No. 5,985,352 (see, e.g., col. 31, line 37-col. 32, line 21).

In some embodiments, the computer system that is capable of executing the computer-implemented methods herein comprises a processor, a fixed storage medium (i.e., a hard drive), system memory (e.g., RAM and/or ROM), a keyboard, a display (e.g., a monitor), a data input device (e.g., a device capable of providing raw or transformed microarray data to the system), and optionally a drive capable of reading and/or writing computer-readable media (i.e., removable storage, e.g., a CD or DVD drive). The system optionally also comprises a network input/output device and a device allowing connection to the internet.

In some embodiments the computer-readable instructions (e.g., a computer software product) enabling the system to carry out any of the methods described herein (i.e. software for carry out any of the method steps described herein) are encoded on the fixed storage medium and enable the system to display results to a user, or to provide results to a second set of computer-readable instructions (i.e., a second program), or to send the results to a data structure residing on the fixed storage medium or to another network computer or to a remote location through the internet.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: Pilot Study

Upon selection of directly observed variants, selection of candidate regions of genomic DNA containing the selected directly observed variants, and after a probe set was selected as described herein, a pilot study was performed.

48 samples from the 1KG sample set were selected and accessed samples of their DNA from Coriell (see, world wide web at "coriell.org/1/NHGRI/Collections/1000-Genomes-Collections/1000-Genomes-Project"). For the sake of this example, the 48 samples were considered as if they were completely new, and were processed by the genotyping by sequencing probe set described herein. The results of the genotyping by sequencing of the 48 samples were compared to the control results obtained from whole genome sequencing at 30x coverage (after filtering). The reference panel was considered to be the 1KG WGS data without the 48 samples.

The pilot set of samples were chosen to be diverse. One sample failed to have enough DNA to sequence and was eliminated, thus leaving 47 samples for testing. The samples are summarized in Table 1.

TABLE 1

Diversity of the 47 Samples used in the Pilot Study from 1 KG

| Continent | Population | Count |
|---|---|---|
| Africa | Asan | 4 |
| Africa | Gambian Mandinka | 4 |
| Africa | Luhya | 4 |
| America | Peruvian | 4 |
| America | Mexican Ancestry | 4 |
| Asia | Han Chinese | 3 |
| Asia | Punjabi | 4 |
| Europe | British | 5 |
| Europe | Finnish | 5 |
| Europe | Iberian | 5 |
| Europe | Toscani | 5 |

Each row is for a population in the 1KG and the count of samples from that region.

A first aim was to determine how well the probes work in practice (i.e., whether the probe set captures sequences that are specific to the intended location in the genome). Two reasons were considered for eliminating particular probes from an initial probe set: 1) having too low coverage at variants such that some DNA samples were not generating a signal; and 2) having shown that many reads that did not map easily to the genome where captured by that probe. An overall goal was to eliminate probes that result in inefficient capturing and eliminating probes that are not providing a sufficient signal for desired variants. Many probes fell into both categories. As a result, about 14,000 probes were identified that were obtaining too low coverage.

Computational experiments were performed that showed that the eliminated probes do not make a major difference to the performance of the overall imputation, where the data was observed by filtering the WGS experiments to represent what could be observed.

Another aim was to determine whether the information retrieved from the sequencing reads was able to aid the directly observed variants and enable imputation of other variants. To assess the accuracy of imputation, two processes were performed: 1) from the variants called, variants close to or in eliminated probes were eliminated; and 2) the remaining called variants were processed to return imputed variants (for all estimated 15 million variants).

Data Preparation Methods—Variant Calls to Imputation:

To perform imputation on the pilot samples, a new reference set of haplotypes was used. The reference was the 1KG WGS data set with the pilot samples removed. This new reference data was then used twice: 1) by the program GLIMPSE for improved variant calling and phasing, and 2) by the program Minimac3 for variant imputation. The imputed variant calls were then compared to the directly observed variant calls from the whole genome sequencing.

Assessing Imputation Quality:

To assess imputation quality, the square of the correlation between the directly observed genotype and the imputed genotype was assessed. This metric is commonly referred to as "Imputation Rsq" or "$r^2$ measure" or "r-squared" which is the squared correlation coefficient between a true genotype and its experimentally derived counterpart, as estimated from imputation. When r2 is 1.0, the two are identical. When it is near 0.0, the experimentally derived counterpart is no better than a blind estimate. Specifically, a genotype vector of directly observed genotypes was created from the whole genome sequencing data, where: if the genotype was for two reference alleles, it was encoded as a 0; if the genotype was for one reference and one alternative allele, it was encoded as a 1; and if the genotype was for two reference alleles, it was encoded as a 2. For the vector of imputed genotypes, it was different because each of the three states have a probability. For example, there may be a 80% probability of being a 0, a 20% probability of being a 1, and a 0% probability of being a 2. For the vector of imputed genotypes, the expected genotype was returned which was 0.2, from 0.8*0+0.2*1+0*2.

A Pearson' correlation coefficient was performed on the two vectors. The fact that there are only 47 samples for each genotype was noted. To enable a better measure across variants, variants were pool together by allele frequency (so that they all have the same expected genotype) and the correlation on the vector across samples and variants was performed. This process for imputation Rsq followed standard approaches.

FIG. 1 shows imputation Rsq for difference frequency bins from imputation from different observed data. The highest correlation (and best imputation) occurred when the whole genome sequencing was filtered to observe just variants in the chosen probe regions. The line thus formed represented the best performance sought. The blue line represents the directly assayed global screening array for these samples (run in-house under normal protocols). It was desired that the imputation from the pilot study to be at least as good as the global screening array. The green line represents the imputation quality of the directly observed genotyping-by-sequencing design, after the processing described herein. The genotyping-by-sequencing design considerably out-performed the global screening array and was close to the sought best performance, given the probes selected. This pilot study has shown that the genotyping-by-sequencing design can out-perform the global screening array for a reasonable cost. The pilot study was not just a simulation study but a direct comparison between the performance from the two assays from DNA sample to imputation comparison. Finally, the genotyping-by-sequencing design was compared to the very large array called the MEGA array (the Multi-Ethnic Genotyping Array), which has three times more variants than the global screening array. When that array was simulated by perfectly observing all variants it assays from the whole genome sequencing version of the pilot data, the genotyping-by-sequencing design performed similarly to the best the MEGA array would be. In practice, the MEGA array would have less performance. The genotyping-by-sequencing design had similar performance to the MEGA array, all at a cost that is comparable to the global screening array (which is three times smaller than the MEGA array). Accordingly, the genotyping-by-sequencing design worked well to provide a very cost-effective strategy to assay genetic information and provide high quality imputation.

Example 2: Genotyping by Sequencing

Figure 2:
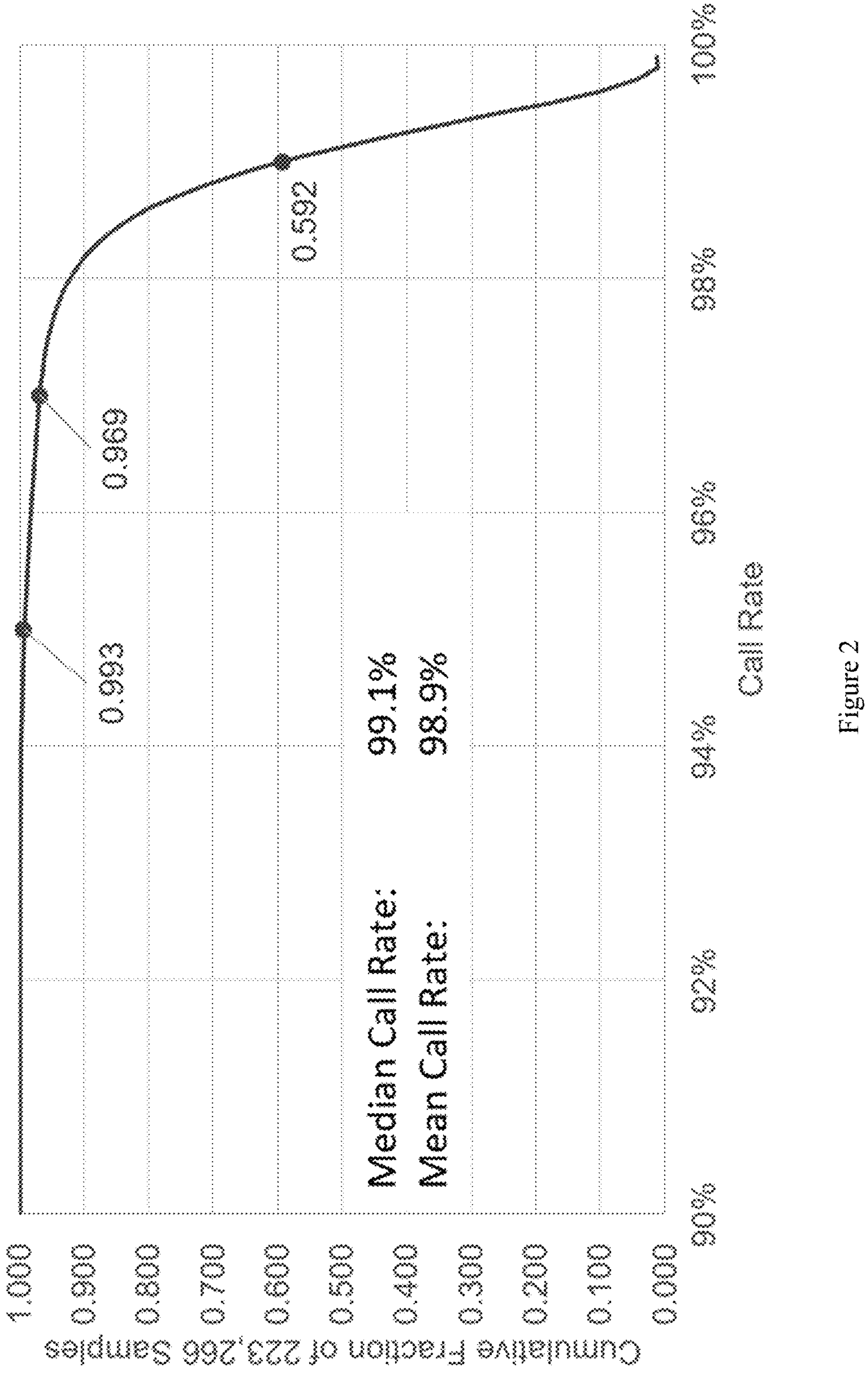
FIG. 2 shows a mean call rate of 98.9%, and 99.3% of samples with a call rate of 95% or greater for a genotyping by sequencing assay run on 223,266 samples, each evaluated at the design sites for coverage, wherein the call rate is the percentage of sites with actionable genotypes.

The Genotyping by Sequencing assay has been successfully run on 223,266 samples, each evaluated at the design sites for coverage. The call rate is the percentage of sites with actionable genotypes. FIG. 2 shows a mean call rate of 98.9%, and 99.3% of samples with a call rate of 95% or greater.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method for manufacturing nucleic acid probes for genotyping by sequencing, the method comprising:

a) selecting a plurality of directly observed genetic variants to capture by the nucleic acid probes;

b) eliminating low confidence variants from the plurality of directly observed genetic variants, thereby producing a filtered plurality of directly observed genetic variants;

c) phasing the filtered plurality of directly observed genetic variants;

d) identifying the presence or absence of one or more proxy variants for each variant within the filtered plurality of directly observed genetic variants;

e) selecting a plurality of candidate regions of genomic DNA comprising the filtered plurality of directly observed genetic variants, wherein each candidate region of genomic DNA comprises from about 25 to about 150 bases, and comprises at least one variant among the filtered plurality of directly observed genetic variants;

f) calculating a Quality score for each candidate region of genomic DNA that estimates the capture efficiency and alignment success of a probe;

g) calculating a Probe score for each candidate region of genomic DNA by multiplying the Quality score by the number of variants captured by the candidate region of genomic DNA, wherein the number of variants captured by the candidate region of genomic DNA is the sum of the number of directly observed variants captured by the candidate region of genomic DNA and the number of corresponding proxy variants in different candidate regions of genomic DNA;

h) selecting one or more candidate regions of genomic DNA having the highest Probe score for inclusion in a final set of regions of genomic DNA;

i) repeating steps g) and h) on unselected candidate regions of genomic DNA for inclusion in the final set of regions of genomic DNA, wherein the number of variants in the unselected candidate region of genomic DNA is the sum of: 1) the number of directly observed variants in the unselected candidate region of genomic DNA excluding any directly observed variant within a previously selected region of genomic DNA, and 2) the number of corresponding proxy variants in different candidate regions of genomic DNA excluding any proxy variant corresponding to a directly observed variant within a previously selected region of genomic DNA, wherein steps g) and h) are repeated until a maximum number of regions of genomic DNA has been selected; and j) generating a set of nucleic acid probes complementary to the nucleic acid sequence of each of the genomic regions among the final set of regions of genomic DNA.

2. A method for genotyping a DNA sample by sequencing, the method comprising:

a) hybridizing a set of nucleic acid probes manufactured according to claim 1 to the DNA sample to generate probe-hybridized genomic DNA;

b) sequencing the probe-hybridized genomic DNA to produce a plurality of sequencing reads corresponding to genomic regions captured by the set of nucleic acid probes;

c) mapping the plurality of sequencing reads to a reference genome;

d) calling the directly observed variants present in the mapped sequencing reads obtained in step c), wherein the directly observed variants comprise variants captured by hybridization of the set of nucleic acid probes and subsequently sequenced; and e) imputing, based on the presence of directly observed variants identified in step d), unobserved variants from genomic regions of the DNA sample not captured by hybridization of the set of nucleic acid probes and not sequenced, thereby establishing a genotype of the sample DNA.

3. The method of claim 2, wherein the DNA sample is obtained from a subject having a disease or condition.

4. The method of claim 2, wherein the DNA sample is obtained from a tumor from a subject.

5. The method of claim 2, wherein probes resulting in less than 8X coverage of the directly observed variants within the plurality of sequencing reads are removed from the set of nucleic acid probes.

6. The method of claim 2, wherein probes resulting in inefficient capturing of the sample DNA are removed from the set of nucleic acid probes.

7. The method of claim 2, wherein the plurality of sequencing reads comprises about 5 million to about 30 million sequencing reads.

8. The method of claim 2, wherein low confidence called variants resulting from low coverage reads are eliminated to produce a final set of called directly observed variants.

9. The method of claim 8, wherein eliminating low confidence called variants comprises imputing the same called directly observed variants from a reference panel of variants.

10. The method of claim 8, further comprising phasing the called directly observed variants into sets of known haplotypes.

11. The method of claim 8, wherein the percentage of called variants having greater than 10X coverage is determined, and re-hybridizing the set of nucleic acid probes to the DNA sample when the percentage of called variants having greater than 10X coverage is less than about 95%.

12. The method of claim 8, wherein called directly observed variants that are close to or in probes eliminated from the set of nucleic acid probes are omitted from the final set of called directly observed variants.

13. The method of claim 2, wherein the unobserved variants are imputed from a reference panel of variants based on the presence of called directly observed variants in the DNA sample.

14. A method for genotyping a DNA sample by sequencing using a set of nucleic acid probes, the method comprising:

a) selecting a plurality of regions of genomic DNA from the DNA sample comprising a plurality of directly observed genetic variants;

b) identifying the set of nucleic acid probes for hybridization to the selected plurality of regions of genomic DNA;

c) hybridizing the set of nucleic acid probes to the DNA sample to generate probe-hybridized genomic DNA;

d) sequencing the probe-hybridized genomic DNA to produce a plurality of sequencing reads corresponding to genomic regions captured by the set of nucleic acid probes;

e) mapping the plurality of sequencing reads to a reference genome;

f) calling the directly observed variants present in the mapped sequencing reads obtained in step e), wherein the directly observed variants comprise variants captured by hybridization of the set of nucleic acid probes and subsequently sequenced; and g) imputing, based on the presence of directly observed variants identified in step f), unobserved variants from genomic regions of the DNA sample not captured by hybridization of the set of nucleic acid probes and not sequenced, thereby establishing a genotype of the sample DNA.

15. The method of claim 14, wherein the set of nucleic acid probes is identified by selecting a plurality of candidate regions of genomic DNA comprising the directly observed genetic variants, wherein each candidate region of genomic DNA comprises from about 25 to about 150 bases, and comprises at least one variant among the plurality of directly observed genetic variants.

16. The method of claim 14, wherein the set of nucleic acid probes comprises from about 500,000 to about 700,000 probes.

17. The method of claim 14, wherein probes resulting in less than 8X coverage of the directly observed variants within the plurality of sequencing reads are removed from the set of nucleic acid probes.

18. The method of claim 14, wherein probes resulting in inefficient capturing of the sample DNA are removed from the set of nucleic acid probes.

19. The method of claim 14, wherein the plurality of sequencing reads comprises about 5 million to about 30 million sequencing reads.

20. The method of claim 14, wherein low confidence called variants resulting from low coverage reads are eliminated to produce a final set of called directly observed variants.

21. The method of claim 20, wherein eliminating low confidence called variants comprises imputing the same called directly observed variants from a reference panel of variants.

22. A system comprising:

a data processor having a memory coupled thereto, wherein the memory comprises programs including instructions for:

selecting a plurality of regions of genomic DNA from a DNA sample comprising a plurality of directly observed genetic variants;

identifying a set of nucleic acid probes for hybridization to the selected plurality of regions of genomic DNA, and sending instructions to an oligonucleotide synthesizer for synthesis of the set of the nucleic acid probes;

receiving a plurality of sequencing reads from the DNA sequencing apparatus produced from sequencing the generation of probe-hybridized genomic DNA upon hybridization of the set of the nucleic acid probes to a DNA sample, wherein the sequencing reads correspond to genomic regions captured by hybridization of the set of nucleic acid probes;

mapping the plurality of sequencing reads to a reference genome;

calling the directly observed variants present in the mapped sequencing reads obtained in the mapping step, wherein the directly observed variants comprise variants captured by hybridization of the set of nucleic acid probes and subsequently sequenced; and imputing, based on the presence of directly observed variants called from the mapped sequencing reads, unobserved variants from genomic regions of the DNA sample not captured by hybridization of the set of nucleic acid probes and not sequenced, thereby establishing a genotype of the sample DNA.

* * * * *